(12) United States Patent
Villa et al.

(10) Patent No.: US 7,410,652 B2
(45) Date of Patent: *Aug. 12, 2008

(54) CONTROLLED RELEASE AND TASTE MASKING ORAL PHARMACEUTICAL COMPOSITION

(75) Inventors: Roberto Villa, Lecco (IT); Massimo Pedrani, Cignese (IT); Mauro Ajani, Milan (IT); Lorenzo Fossati, Milan (IT)

(73) Assignee: Cosmo Technologies Limited, Wicklow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 11/378,378

(22) Filed: Mar. 20, 2006

(65) Prior Publication Data

US 2006/0159749 A1    Jul. 20, 2006

Related U.S. Application Data

(62) Division of application No. 10/009,532, filed as application No. PCT/EP00/05356 on Jun. 9, 2000.

(30) Foreign Application Priority Data

Jun. 14, 1999 (IT) .............................. MI99A1317
Mar. 3, 2000 (IT) .......................... MI2000A0422

(51) Int. Cl.
  *A61K 9/22* (2006.01)
  *A61K 9/20* (2006.01)
  *A61K 9/26* (2006.01)
  *A61K 9/48* (2006.01)

(52) U.S. Cl. ...................... 424/468; 424/451; 424/464; 424/465; 424/469; 424/470

(58) Field of Classification Search ................. 424/451, 424/464

See application file for complete search history.

(56) References Cited

U.S. PATENT DOCUMENTS

| 5,342,625 A | * | 8/1994 | Hauer et al. |
| 5,597,844 A | | 1/1997 | Chauhan et al. |
| 6,190,692 B1 | * | 2/2001 | Busetti et al. |
| 6,368,635 B1 | | 4/2002 | Akiyama et al. |

FOREIGN PATENT DOCUMENTS

| DE | 41 31 562 A1 | | 3/1993 |
| EP | 0 514 008 | | 11/1992 |
| EP | 0 514 008 A1 | | 11/1992 |
| GB | 935639 | | 9/1963 |
| WO | 96/13273 | * | 5/1996 |
| WO | WO 99/11245 | | 3/1999 |
| WO | WO 99/17752 | | 4/1999 |

* cited by examiner

*Primary Examiner*—Humera N Sheikh
(74) *Attorney, Agent, or Firm*—Young & Thompson

(57) ABSTRACT

Controlled release and taste masking compositions containing one or more active principles inglobated in a three-component matrix structure, i.e. a structure formed by successive amphiphilic, lipophilic or inert matrices and finally inglobated or dispersed in hydrophilic matrices. The use of a plurality of systems for the control of the dissolution of the active ingredient modulates the dissolution rate of the active ingredient in aqueous and/or biological fluids, thereby controlling the release kinetics in the gastrointestinal tract.

4 Claims, No Drawings

CONTROLLED RELEASE AND TASTE MASKING ORAL PHARMACEUTICAL COMPOSITION

The present invention relates to controlled release and taste-masking compositions containing mesalamine (5-aminosalicylic acid) incorporated in a three-component matrix structure, i.e. a structure formed by successive amphiphilic, lipophilic or inert matrices and finally incorporated or dispersed in hydrophilic matrices. The use of a plurality of systems for the control of the dissolution of the active ingredient modulates the dissolution rate of the active ingredient in aqueous and/or biological fluids, thereby controlling the release kinetics in the gastrointestinal tract, and it also allows the oral administration of active principles having unfavourable taste characteristics or irritating action on the mucosae of the administration site, particularly in the buccal area. The compositions are suitable to the oral administration or for acting topically at some areas of the gastrointestinal tract.

TECHNOLOGICAL BACKGROUND

The preparation of a sustained, controlled, delayed or anyhow modified release form can be carried out according to different known techniques: 1. The use of inert matrices, in which the main component of the matrix structure opposes some resistance to the penetration of the solvent due to the poor affinity towards aqueous fluids; such property being known as lipophilia. 2. The use of hydrophilic matrices, in which the main component of the matrix structure opposes high resistance to the progress of the solvent, in that the presence of strongly hydrophilic groups in its chains, mainly branched, remarkably increases viscosity inside the hydrated layer 3. The use of bioerodible matrices, which are capable of being degraded by the enzymes of some biological compartment. All the procedures listed above suffer, however, from drawbacks and imperfections.

Inert matrices, for example, generally entail nonlinear, but esponential, release of the active ingredient.

Hydrophilic matrices have a linear behaviour until a certain fraction of active ingredient has been released, then they significantly deviate from linear release.

Bioerodible matrices are ideal to carry out the socalled "site-release", but they involve the problem of finding the suitable enzyme or reactive to degradation.

Furthermore, they frequently release in situ metabolites that are not wholly toxicologically inert. A number of formulations based on inert lipophilic matrices have been described: Drug Dev. Ind. Pharm. 13 (6), 1001-1022, (1987) discloses a process making use of varying amounts of colloidal silica as a porization element for a lipophilic inert matrix in which the active ingredient is incorporated.

The same notion of canalization of an inert matrix is described in U.S. Pat. No. 4,608,248 in which a small amount of a hydrophilic polymer is mixed with the substances forming an inert matrix, in a non sequential compenetration of different matrix materials.

EP 375,063 discloses a technique for the preparation of multiparticulate granules for the controlled-release of the active ingredient which comprises co-dissolution of polymers or suitable substances to form a inert matrix with the active ingredient and the subsequent deposition of said solution on an inert carrier which acts as the core of the device. Alternatively, the inert carrier is kneaded with the solution containing the inert polymer and the active ingredient, then the organic solvent used for the their dissolution is evaporated off to obtain a solid residue.

The resulting structure is a "reservoir", i.e. is not macroscopically homogeneous along all the symmetry axis of the final form.

The same "reservoir" structure is also described in Chem. Pharm. Bull. 46 (3), 531-533, (1998) which improves the application through an annealing technique of the inert polymer layer which is deposited on the surface of the pellets. To the "reservoir" structure also belong the products obtained according to the technique described in WO 93/00889 which discloses a process for the preparation of pellets in hydrophilic matrix which comprises:—dissolution of the active ingredient with gastro resistant hydrophilic polymers in organic solvents;—drying of said suspension;—subsequent kneading and formulation of the pellets in a hydrophilic or lipophilic matrix without distinction of effectiveness between the two types of application.

EP 0 453 001 discloses a multiparticulate with "reservoir" structure inserted in a hydrophilic matrix. The basic multiparticulate utilizes two coating membranes to decrease the release rate of the active ingredient, a pH-dependent membrane with the purpose of gastric protection and a pH-independent methacrylic membrane with the purpose of slowing down the penetration of the aqueous fluid. WO 95/16451 discloses a composition only formed by a hydrophilic matrix coated with a gastro-resistant film for controlling the dissolution rate of the active ingredient. When preparing sustained-, controlled-release dosage forms of a medicament topically active in the gastrointestinal tract, it is important to ensure a controlled release from the first phases following administration, i.e. when the inert matrices have the maximum release rate inside the logarithmic phase, namely the higher deviation from linear release.

Said object has been attained according to the present invention, through the combination of an amphiphilic matrix inside an inert matrix, the latter formulated with a lipophilic polymer in a superficial hydrophilic matrix. The compositions of the invention are characterized by the absence of a first phase in which the medicament superficially present on the matrix is quickly solubilized, and by the fact the amphiphilic layer compensate the lack of affinity of the aqueous solvent with the lipophilic compounds forming the inner inert matrix.

DISCLOSURE OF THE INVENTION

The invention provides controlled release and taste masking oral pharmaceutical compositions containing mesalamine, comprising:
  a) a matrix consisting of lipophilic compounds with melting point lower than 90 C and optionally by amphiphilic compounds in which the active ingredient is at least partially incorporated;
  b) optionally an amphiphilic matrix;
  c) an outer hydrophilic matrix in which the lipophilic matrix and the optional amphiphilic matrix are dispersed;
  d) optionally other excipients.

A particular aspect of the invention consists of controlled release oral compositions containing mesalamine, comprising:
  a) a matrix consisting of amphiphilic compounds and lipophilic compounds with melting point below 90 C in which the active ingredient is at least partially incorporated;
  b) an outer hydrophilic matrix in which the lipophilic/amphiphilic matrix is dispersed;
  c) optional other excipients.

A further aspect of the invention provides taste masking oral pharmaceutical compositions containing mesalamine, comprising:

- an inert or lipophilic matrix consisting of C6 C20 alcohols or C8-C20 fatty acids or esters of fatty acids with glycerol or sorbitol or other polyalcohols with carbon atom chain not higher than six;
- an amphiphilic matrix consisting of polar lipids of type I or II or glycols partially etherified with C1-C4 alkyl chains;
- an outer hydrophilic matrix containing the above matrices, mainly formed by saccharide, dextrin, polyalcohol or cellulose compounds or by hydrogels;
- optional excipients to give stability to the pharmaceutical formulation.

DETAILED DISCLOSURE OF THE INVENTION

The compositions of the invention can be prepared by a method comprising the following steps:

a) the active ingredient is first inglobated by simple kneading or mixing in a matrix or coating consisting of compounds having amphiphilic properties, which will be further specified below. The active principle (s) can be mixed with the amphiphilic compounds without the aid of solvents or with small amounts of water-alcoholic solvents.

b) The matrix obtained in a) is incorporated in a low melting lipophilic excipient or mixture of excipients, while heating to soften and/or melt the excipient itself, which thereby incorporates the active ingredient by simple dispersion. After cooling at room temperature an inert matrix forms, which can be reduced in size to obtain inert matrix granules containing the active ingredient particles.

c) The inert matrix granules are subsequently mixed together with one or more hydrophilic water-swellable excipients. The mixture is then subjected to compression or tabletting. This way, when the tablet is contacted with biological fluids, a high viscosity swollen layer is formed, which coordinates the solvent molecules and acts as a barrier to penetration of the aqueous fluid itself inside the new structure. Said barrier antagonizes the starting "burst effect" caused by the dissolution of the medicament inglobated inside the inert matrix, which is in its turn inside the hydrophilic matrix.

The amphiphilic compounds which can be used according to the invention comprise polar lipids of type I or II (lecithin, phosphatidylcholine, phosphatidylethanolamine), ceramides, glycol alkyl ethers such as diethylene glycol monomethyl ether(Transcutol (R)).

The lipophilic matrix consists of substances selected from unsaturated or hydrogenated alcohols or fatty acids, salts, esters or amides thereof, fatty acids mono-, di- or triglycerides, the polyethoxylated derivatives thereof, waxes, ceramides, cholesterol derivatives or mixtures thereof having melting point within the range of 40 to 90 C, preferably from 60 to 70 C.

If desired, a fatty acid calcium salt may be incorporated in the lipophilic matrix which is subsequently dispersed in a hydrophilic matrix prepared with alginic acid, thus remarkably increasing the hydrophilic matrix viscosity following penetration of the solvent front until contact with the lipophilic matrix granules dispersed inside.

According to an embodiment of the invention, an amphiphilic matrix with high content in active ingredient, typically from 5 to 95% w/w, is first prepared by dispersing the active ingredient or the mixture of active ingredients in a mixture of amphiphilic compounds, such as lecithin, other type II polar lipids, surfactants, or in diethylene glycol monoethyl ether; the resulting amphiphilic matrix is then mixed or kneaded, usually while hot, with lipophilic compounds suitable to form an inert matrix, such as saturated or unsaturated fatty acids, such as palmitic, stearic, myristic, lauric, laurylic, or oleic acids or mixtures thereof with other fatty acids with shorter chain, or salts or alcohols or derivatives of the cited fatty acids, such as mono-, di-, or triglycerides or esters with polyethylene glycols, alone or in combination with waxes, ceramides, cholesterol derivatives or other apolar lipids in various ratios so that the melting or softening points of the lipophilic compounds mixtures is within the range of 40 to 90 C, preferably from 60 to 70 C. Alternatively, the order of formation of the inert and amphiphilic matrices can be reversed, incorporating the inert matrix inside the amphiphilic compounds.

The resulting inert lipophilic matrix is reduced into granules by an extrusion and/or granulation process, or any other known processes which retain the homogeneous dispersion and matrix structure of the starting mixture.

The hydrophilic matrix consists of excipients known as hydrogels, i.e. substances which when passing from the dry state to the hydrated one, undergo the so-called "molecular relaxation", namely a remarkable increase in mass and weight following the coordination of a large number of water molecules by the polar groups present in the polymeric chains of the excipients themselves.

Examples of hydrogels which can be used according to the invention are compounds selected from acrylic or methacrylic acid polymers or copolymers, alkylvinyl polymers, hydroxyalkyl celluloses, carboxyalkyl celluloses, polysaccharides, dextrins, pectins, starches and derivatives, natural or synthetic gums, alginic acid.

In case of taste-masking formulations, the use of polyalcohols such as xylitol, maltitol and mannitol as hydrophilic compounds can also be advantageous.

The lipophilic matrix granules containing the active ingredient are mixed with the hydrophilic compounds cited above in a weight ratio typically ranging from 100:0.5 to 100:50 (lipophilic matrix:hydrophilic matrix). Part of the active ingredient can optionally be mixed with hydrophilic substances to provide compositions in which the active ingredient is dispersed both in the lipophilic and the hydrophilic matrix, said compositions being preferably in the form of tablets, capsules and/or minitablets.

The compression of the mixture of lipophilic and/or amphiphilic matrix, hydrogel-forming compound and, optionally, active ingredient not inglobated in the lipophilic matrix, yields a macroscopically homogeneous structure in all its volume, namely a matrix containing a dispersion of the lipophilic granules in a hydrophilic matrix. A similar result can also be obtained by coating the lipophilic matrix granules with a hydrophilic polymer coating.

The tablets obtainable according to the invention can optionally be subjected to known coating processes with a gastro-resistant film, consisting of, for example, methacrylic acids polymers(Eudragit (R)) or cellulose derivatives, such as cellulose acetophthalate.

The compositions of the invention can further contain conventional excipients, for example bioadhesive excipients such as chitosans, polyacrylamides, natural or synthetic gums, acrylic acid polymers.

The compositions of the invention can contain more than one active ingredient, each of them being optionally contained in the hydrophilic matrix or in the inert amphiphilic matrix, and are preferably in the form of tablets, capsules or minitablets.

In terms of dissolution characteristics, contact with water or aqueous fluids causes the immediate penetration of water inside the more superficial layer of the matrix which, thanks to the presence of the aqueous solvent, swells due to the distension of the polymeric chains of the hydrogels, giving rise to a high viscosity hydrated front which prevents the further penetration of the solvent itself linearly slowing down the dissolution process to a well determined point which can be located at about half the thickness, until the further penetration of water would cause the disintegration of the hydrophilic layer and therefore the release of the content which, consisting of inert matrix granules, however induces the diffusion mechanism typical of these structures and therefore further slows down the dissolution profile of the active ingredient.

The presence of the amphiphilic matrix inside the lipophilic matrix inert allows to prevent any unevenness of the release profile of the active ingredient. The surfactants present in the amphiphilic portion promote wettability of the porous canaliculuses which cross the inert matrix preventing or reducing resistance to penetration of the solvent inside the inert matrix.

To obtain taste masking tablets, the components of the hydrophilic matrix are carefully selected to minimize the active substance release time through penetration accelerated by the canalization induced by the hydrophilic compound.

The following Example illustrate the invention in greater detail.

EXAMPLE 1

500 g of 5-aminosalicylic acid and 20 g of octylonium bromide are mixed with 10 g of soy lecithin dissolved in 50 g of a water:ethyl alcohol 1:3 mixture at about 50 C.

After homogenization and drying, the granules of the resulting matrix are treated in a kneader with 20 g of carnauba wax and 50 g of stearic acid, heating until homogeneous dispersion, then cold-extruded into small granules. The inert matrix granules are loaded into a mixer in which 30 g of carbopol 971 P and 65 g of hydroxypropyl methylcellulose are sequentially added. After a first mixing step for homogeneously dispersing the powders, 60 g of microcrystalline cellulose and 5 g of magnesium stearate are added. After mixing, the final mixture is tabletted to unitary weight of 760 mg/tablet. The resulting tablets are film-coated with cellulose acetophthalate or polymethacrylates and a plasticizer to provide gastric resistance and prevent the early release of product in the stomach.

The resulting tablets, when subjected to dissolution test in simulated enteric juice, have shown a release of the active principles having the following profile: after 60 minutes no more than 30%, after 180 minutes no more than 60%, after 5 hours no more than 80%.

The invention claimed is:

1. A controlled release oral pharmaceutical composition in a tablet form containing mesalamine as the active ingredient, consisting essentially of:
    a) a matrix, consisting of lipophilic compounds with a melting point lower than 90° C. in which the active ingredient is at least partially dispersed, said lipophilic compounds being a combination of at least one wax and at least one saturated fatty acid or unsaturated fatty acid;
    b) a hydrophilic matrix in which the lipophilic matrix is dispersed, said hydrophilic matrix consisting of carboxyalkylcellulose; and
    c) a matrix consisting of amphiphilic compounds being selected from the group consisting of polar lipids of type I, polar lipids of type II and glycols partially etherified with C1-C4 alkyl chains, in which the active ingredient is at least partially dispersed, said matrix of amphiphilic compounds being dispersed in the hydrophilic matrix, wherein,
    the matrix of lipophilic compounds, the matrix of hydrophilic compounds, and the matrix of amphiphilic compounds, in combination, provide controlled release.

2. The composition as claimed in claim 1, wherein the saturated fatty acid is selected from the group consisting of palmitic, stearic, myristic, lauric, laurilic or oleic acids, and mixtures thereof.

3. The composition as claimed in claim 1, wherein the saturated fatty acid is stearic acid.

4. The composition as claimed in claim 1, wherein the melting point of the lipophilic matrix is from 40° C. to 90° C.

* * * * *